(12) United States Patent
Van Driessche et al.

(10) Patent No.: US 7,910,782 B2
(45) Date of Patent: Mar. 22, 2011

(54) COBALT RECOVERY FROM COBALT CATALYSED HYDROFORMYLATION REACTIONS

(75) Inventors: Eddy T. A. Van Driessche, Eeklo (BE); Arie Van Vliet, Stevvebeek (BE); Raphael Frans Caers, Edegem (BE); Hubertus Joseph Beckers, Keerbergen (BE); Ronald Dean Garton, Wezembeek-Oppem (BE); Bertrand Raymond Da Cruz, Lambersart (FR); Michel J. P. Lepagnol, Mont Saint Aignan (FR); Edwin Kooke, Ridderkerk (NL)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/532,475

(22) PCT Filed: Mar. 28, 2008

(86) PCT No.: PCT/EP2008/053718
§ 371 (c)(1),
(2), (4) Date: Mar. 5, 2010

(87) PCT Pub. No.: WO2008/122526
PCT Pub. Date: Oct. 16, 2008

(65) Prior Publication Data
US 2010/0228046 A1  Sep. 9, 2010

(30) Foreign Application Priority Data

Apr. 10, 2007 (GB) .................................. 0706887.7

(51) Int. Cl.
*C07C 45/50* (2006.01)
*C07C 29/16* (2006.01)
*C07C 67/08* (2006.01)
*C07C 67/303* (2006.01)

(52) U.S. Cl. .......... 568/882; 568/909; 568/451; 560/98; 560/127

(58) Field of Classification Search .................. 568/882, 568/909, 451; 560/98, 127
See application file for complete search history.

(56) References Cited

U.S. PATENT DOCUMENTS

| | | |
|---|---|---|
| 3,188,351 A | 6/1965 | Lemke |
| 4,041,057 A | 8/1977 | Fanning |
| 5,091,599 A | 2/1992 | De Munck et al. |
| 5,130,107 A | 7/1992 | De Munck et al. |
| 5,336,473 A | 8/1994 | Nadler et al. |
| 5,585,524 A | 12/1996 | Sielcken et al. |
| 6,437,170 B1 | 8/2002 | Thil et al. |

FOREIGN PATENT DOCUMENTS

| | | |
|---|---|---|
| CN | 1184858 | 6/1998 |
| FR | 2 480 276 | 10/1981 |
| SU | 372199 | 4/1971 |
| SU | 992505 | 6/1981 |
| WO | WO 2005/058782 | 6/2005 |
| WO | WO 2005/058787 | 6/2005 |

*Primary Examiner* — Sikarl A Witherspoon
(74) *Attorney, Agent, or Firm* — Leandro Arechederra, III

(57) ABSTRACT

In a hydroformylation reaction, the circulation and recovery of cobalt carbonyl in a cobalt catalyst cycle using carbonylate as an intermediate and acidification thereof, is improved by supplying an aqueous sulfuric acid solution containing less than 16% wt of sulfuric acid to the carbonylate to control sulfuric acid concentration in the carbonylate/acid mixture, before accounting for any acid consuming reaction, to a value of from 2% to 10% by weight. Single step and multistage liquid/liquid extraction techniques as well as vapor/liquid extraction techniques followed by the absorption of cobalt from the vapor in an organic liquid both benefit from this improvement.

14 Claims, 1 Drawing Sheet

COBALT RECOVERY FROM COBALT CATALYSED HYDROFORMYLATION REACTIONS

CROSS REFERENCE TO RELATED APPLICATIONS

This application is a 371 National Stage Application of International Application No. PCT/EP2008/053718, filed Mar. 28, 2008, which claims the benefit of GB 0706887.7, filed Apr. 10, 2007, the disclosures of which are herein incorporated by reference in their entireties.

FIELD OF THE INVENTION

The present invention relates to the recovery of cobalt from cobalt catalysed hydroformylation reactions.

BACKGROUND

Hydroformylation is a well-known process in which an olefin is reacted with carbon monoxide and hydrogen in the presence of a catalyst to form aldehydes and alcohols containing one carbon atom more than the feed olefin. This process has been operated commercially for many years and there have been two principal technology families used. One is known as the low or medium pressure oxo process family, which generally involves the use as catalyst of an organometallic complex of rhodium with organophosphorous ligands for providing the necessary stability at the lower pressures, and operates at pressures from 10 to 50 bar. The second process family is known as the high or medium-pressure process family and generally involves the use of a cobalt or rhodium based catalyst and typically operates at pressures from 50 to 350 bar. Generally the low pressure processes are used for the hydroformylation of unbranched and terminal, primarily lower olefins such as ethylene, propylene and n-butenes, but also including n-hexene-1, n-octene-1 and mixtures of higher carbon number terminal olefins produced by the Fischer-Tropsch process. The high or medium pressure processes are primarily used for the hydroformylation of linear internal and branched higher olefins such as those containing 5 or more carbon atoms. This process is widely used to produce what are known as "higher alcohols" or aldehydes or acids which are in the $C_6$ to $C_{15}$ range, particularly the $C_9$ to $C_{13}$ range. Such materials are typically used in the production of plasticiser or lubricant esters such as the esters of phthalic acid and anhydride, esters of cyclohexane mono- or dicarboxylic acids, esters of adipic or trimellitic acid, esters of the various isomers of pyromellitic acid, and polyol esters; the alcohols are also used in surfactant derivatives like ethoxylates, sulphates, or ethoxysulfates.

Hydroformylation is typically performed in large volume reactors which may be continuous or batch reactors.

The present invention is concerned with improving the recovery of cobalt from hydroformylation reactions operating continuously and at high or medium pressures and using a cobalt based catalyst.

As with most large scale industrial chemical processes, improvements in the efficiency of the use of raw materials, optimisation of the recycle of unreacted materials and the optimisation of reaction conditions, material balance and other variables are most important. Improvements which can result in a few percentage point increases in conversion, output and efficiency are extremely significant improvements. In certain reactions, such as those employing heavier metals such as cobalt, metal recovery is important for both economic and environmental reasons. Over the years the throughput of cobalt catalysed hydroformylation reactors has considerably increased. This in turn has led to higher cobalt concentrations in the reaction products which has increased the needs for cobalt recovery. For example, cobalt recovery from a stream containing as much as 30,000 ppm cobalt down to 10 ppm or even lower may now be required.

High and medium pressure hydroformylation (sometimes known as OXO) reactions involve the reaction of liquid materials with normally gaseous materials which are at least partly dissolved in the liquid during reaction due to the high pressure conditions, and gaseous materials may also be entrained as droplets or bubbles in the liquid phase. Unreacted gaseous materials are vented off after the reaction. WO 2005/058787 describes a process which is particularly concerned with the optimisation of gas utilisation by the use of a combination of fresh gaseous feeds and recycle gasses to optimise reaction conditions and thus the conversion and yield of the hydroformylation reaction. This process is beneficially employed together with the cobalt recovery techniques of the present invention.

The starting liquids that are involved in high pressure hydroformylation comprise olefins which may be mixtures of olefins such as those obtained from olefin oligomerisation units. For example the olefins may be mixtures of $C_5$ to $C_{12}$ olefins obtained by the phosphoric acid catalysed oligomerisation of $C_3$ and $C_4$ olefins and mixtures thereof, and where olefin mixtures are used, they may have been fractionated to obtain relatively narrow boiling cut mixtures of mostly the appropriate carbon number for the production of aldehydes and alcohols with the desired carbon number. Alternatively the olefins may be obtained by other oligomerisation techniques such as for example the dimerisation or trimerisation of butene using a nickel or nickel oxide catalyst, like the Octol® process or the process described in U.S. Pat. No. 6,437,170, or an oligomerisation process for ethylene, propylene and/or butenes using a nickel salt and involving dialkyl aluminium halides, like the range of Dimersol® processes, or a zeolite or a molecular sieve catalyst. The olefins may also be obtained from ethylene growth processes, in which case they are often called linear alpha olefins or normal alpha olefins and they may have $C_6$, $C_8$, $C_{10}$ or $C_{12}$, or even higher carbon numbers such as up to $C_{14}$, $C_{16}$, $C_{18}$ or even $C_{20}$, or they can be mixtures obtained from the Fischer Tropsch process, which primarily contain terminal olefins but which may show some side branches along their longest alkyl chain, and which may also contain some internal olefins, linear and branched. In this case, also the higher carbon numbers may be useful starting liquids. The starting materials for the oligomerisation units may be obtained from fluid catalytic cracking (FCC), from steamcracking of gasses such as ethane and propane, of liquids such as liquefied petroleum gasses (LPG), of naphtha, of gasoil or heavier distillate, or even of whole crude, from oxygenate-to-olefin processes, and from paraffin dehydrogenation processes.

The gases that are involved in high and medium pressure hydroformylation include carbon monoxide and hydrogen, frequently supplied in a mixture that is known as synthesis gas or "syngas". Syngas can be obtained through the use of partial oxidation technology (PDX), or steam reforming (SR), or a combination thereof that is often referred to as autothermal reforming (ATR). It can be generated from almost every carbon containing source material, including methane, natural gas, ethane, petroleum condensates like propane and/or butane, naphtha or other light boiling hydrocarbon liquids, gasoline or distillate-like petroleum liquids, but also including heavier oils and byproducts from various processes including hydroformylation, and even from coal and other solid materials like biomass and waste plastics. When using liquid feeds, a steam reformer may involve a pre-reformer to convert part of the feed to methane before entering the actual reformer reaction.

Hydroformylation reactions may be continuous or batch reactions and the present invention is concerned with the recovery of cobalt from continuous reactions. The continuous reactions generally take place in a series of two or more reactors and in a preferred embodiment, the reactions take place in a series of reactors involving gas lift reactors as lead or front end reactors, more preferably involving loop reactors. Gas lift reactors are reactors wherein liquid mixing and circulation is enhanced by the lifting force of gas bubbles preferentially present in the liquid of one section of the reactor. This section may be a central zone surrounded by a concentric downflowing zone. Any series of reactors may be made up of separate distinct sections within one or a few reaction vessels. Alternatively, one reactor in the series can in itself be made up of different volumes set up in series or in parallel.

The main hydroformylation reaction is the reaction of an olefin with carbon monoxide and hydrogen to produce an aldehyde,

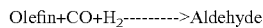

Olefin+CO+H$_2$--------->Aldehyde

There are a number of competing and consecutive reactions, for example:

Olefin+H$_2$--------->Paraffin

Aldehyde+H$_2$----------->Alcohol

Aldehyde+CO+H$_2$----------->Formate ester

Aldehydes can condense with alcohols to form a hemiacetal, R1-CHOH—O—R2, which is not very stable and splits off water to form an unsaturated ether. This again can undergo further reactions:

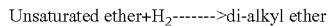

Unsaturated ether+H$_2$------->di-alkyl ether

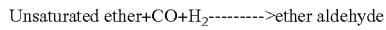

Unsaturated ether+CO+H$_2$--------->ether aldehyde

Aldehydes can also condense with two alcohols to form an acetal, R1-(O—R2)$_2$, while splitting off water. In the above formulae, R1 and R2 independently represent alkyl chains and may be the same or different, unbranched (linear) or branched.

In an industrial hydroformylation plant that is producing alcohols, at least part of the product of hydroformylation which consists primarily of aldehydes, or of mixtures of alcohols, aldehydes and formate esters, potentially together with various other compounds, is hydrogenated to convert the aldehydes and formate esters to alcohols and to reduce the level of the impurities. The hydrogenation reaction is typically operated with a stoichiometric excess of hydrogen.

Preferred conditions for hydrogenation are described in WO 2005/058782, and these conditions are conveniently used in conjunction with the improved cobalt recovery techniques of the present invention.

This invention relates to the recovery of cobalt from such hydroformylation processes and in particular the production of alcohols with cobalt catalysed hydroformylation in a manner in which the amount of waste cobalt is reduced. This brings an economic benefit and also reduces the amount of cobalt in the waste water stream leading to significant environmental benefits. Although not limited thereto, as a preferred operation the techniques of the present invention are used in an overall process employing the hydroformylation process of application WO 2005/058787 and the hydrogenation process of application WO 2005/058782.

In the production of higher alcohols, cobalt catalyst is used for the reaction of the olefins with synthesis gas. After completion of the oxonation reaction, the cobalt catalyst must be removed from the reaction products. For economic reasons the cobalt is recycled for use as the catalyst in the oxonation reaction. For environmental reasons it is important that the level of cobalt in any waste streams be minimized.

Cobalt is a potentially hazardous and expensive material and accordingly there are both environmental and economic benefits to be realized by improving the cobalt recovery from hydroformylation reactions. The present invention provides a cobalt recovery system which is applicable to cobalt streams containing up to 20,000 or even 30,000 ppm by weight of cobalt, whereby at least 99.7% of the cobalt used as hydroformylation catalyst is recovered, and the cobalt content of waste streams is reduced to below 10 ppm, preferably even below 1 ppm wt, more preferably even below 0.5 ppm wt.

The cobalt species that is generally used as a catalyst for hydroformylation is a cobalt carbonyl and is typically hydr(id)ocobalt (tetra)carbonyl, $HCo(CO)_4$. The cobalt catalyst is homogeneous, hence remains in the product of the hydroformylation reaction, and must be removed therefrom and preferably recycled.

Several technologies to remove the cobalt catalyst from the hydroformylation reaction products are known. Examples are the oxidation of the cobalt catalyst, thermally or with air to form cobalt metal or $Co^{2+}$, and preferably in the presence of an acid such as formic or acetic acid to form water soluble $Co^{2+}$ salts such as cobalt formate or acetate. An alternative is the treatment of the hydroformylation product with dilute base such as caustic or soda ash to produce water soluble sodium cobaltcarbonyl. The last method keeps most of the cobalt in its (−1) oxidation state throughout the entire catalyst cycle, and is sometimes referred to as the Kuhlmann catalyst cycle technology and is described in U.S. Pat. No. 3,188,351. It involves two main process steps: first the recovery of the cobalt from the oxo product as an aqueous solution of sodium cobaltcarbonyl, often referred to as "carbonylate", and second the regeneration of hydro cobaltcarbonyl from this carbonylate and the recycle of the hydro cobaltcarbonyl into the feed to hydroformylation. These steps are deployed in combination with techniques for removal and/or recovery of small amounts of cobalt that cannot be recovered by the two main processes. The present invention is concerned with an improvement in this process and in particular to the recovery of cobalt from a carbonylate having a high cobalt content of the water of at least 10,000, but often 20,000 to 30,000 ppm by weight.

The first step of the Kuhlmann Cycle consists of high pressure decobalting in which oil soluble hydro cobaltcarbonyl, which is dissolved in the organic product of hydroformylation and any unreacted organic material such as the olefins, is converted into the water soluble sodium cobaltcarbonyl. This is typically accomplished at high temperature (100-180° C.) and high pressure (160-300 barg) by contacting the oxonation products with a dilute aqueous caustic solution. After cooling and depressuring, the sodium cobaltcarbonyl water (carbonylate) is separated from the organic phase, and, after washing the organic phase with water for removal of residual cobalt, both water phases may be combined. Alternatively, all or part of the water from the washing step may be used as the diluent for the dilute aqueous base in the upstream decobalting step. This reuse brings the benefit of reducing the overall water load of the catalyst system, and reducing the amount of waste water generated by the catalyst cycle, which typically must be treated for, amongst others, dissolved organics, before disposal. The water feedback loop however introduces an additional process interaction which requires a more complex control strategy in order to optimize the overall combined process of decobalting and washing.

In the first step of this decobalting, the reaction of hydro cobaltcarbonyl with caustic is the main reaction. However, a part of the cobalt is present in the oxo product as dicobaltoctacarbonyl ($Co_2(CO)_8$), according to the following equilibrium:

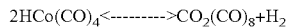

$$2HCo(CO)_4 \longleftrightarrow Co_2(CO)_8 + H_2$$

In the decobalter, as the acidic $HCo(CO)_4$ is neutralised to form its sodium salt, this equilibrium will be shifted to the left. This equilibrium shift competes with the disproportionation reaction of dicobaltoctacarbonyl occurring at the interface of organic and water:

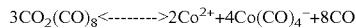

$$3Co_2(CO)_8 \longleftrightarrow 2Co^{2+} + 4Co(CO)_4^- + 8CO$$

From these cobalt species formed, the $Co(CO)_4^-$ anion is recyclable in the downstream acidification step, but the $Co^{2+}$ is not. Therefore, and to the extent dicobaltoctacarbonyl remains in the oxo product, a minor part of the cobalt catalyst is converted into cobalt (II) form, which cannot be recycled back to the olefin feed stream by the conventional means and typically remains in the acidic waste water stream that ultimately needs to be removed from the catalyst cycle. It is therefore preferred to have no or little presence of compounds that promote this disproportionation reaction, such as low molecular weight alcohols, such as ethanol and particularly methanol. In the conventional Kuhlmann cycle, the rate of cobalt (II) formation is minimized by a combination of factors selected from: moderating the contacting intensity of the dilute base with the oxo product in the decobalter, keeping the decobalting residence time and temperature, and the hydrogen and carbon monoxide partial pressures in it, as high as possible, and avoiding large local excesses of caustic or base. Although this reduces the formation of $Co^{2+}$, it does not entirely avoid it.

The $Co^{2+}$ formed may, depending on conditions, stay dissolved in the carbonylate. Upon acidification with sulfuric acid, the sodium cobalt carbonyl is back converted into $HCo(CO)_4$, which can then be removed from the water phase and recycled. The $Co^{2+}$ however stays dissolved as $CoSO_4$, and leaves with the dilute acid stream. Typical cobalt concentrations here may be in the order of 5 to 50 ppm by weight, but depending on alcohol grade and operating conditions also in the order of 60 to 300 ppm by weight. These levels of $Co^{2+}$ may be too high to be disposed of, in which case this remaining cobalt needs to be at least partially recovered. This is typically done by precipitation of the $Co^{2+}$ as $Co(OH)_2$ at a pH of 9.35 or above, preferably 10.5 or above, followed by coagulation and/or flocculation and sedimentation or centrifugation or (ultra)filtration. A pH value above 13.0 is less desirable because then the cobalt hydroxide solubility increases again. Bringing the pH of the sulfuric acid stream up to 10.5 or above consumes a significant amount of base; and the now alkaline waste stream after cobalt precipitation may again need neutralisation before it may be disposed of, both of which are disadvantageous. This tail-end recovery process of $Co^{2+}$, although effective, is therefore a complex and chemical consuming operation. The process typically also requires a high flow of waste water that needs to be treated, thus increasing the amount of acid and base that is required for acidification and subsequent neutralisation, and causing higher burden on any organics cleanup steps.

U.S. Pat. No. 5,130,107 describes an improved process which effectively removes $Co^{2+}$ as cobalt salts, such as cobalt carbonate and cobalt hydroxide, from the carbonylate stream, prior to the contacting with sulphuric acid and stripping, without incurring additional cobalt losses or experiencing operating problems. This is accomplished by precipitation of solid cobalt carbonate, either by using soda ash as the base in the decobalter and/or by assuring sufficient carbon dioxide is present in the decobalter or downstream. When caustic soda is used in the decobalter, sufficient carbon dioxide to also convert all the excess caustic to sodium (bi)carbonate will bring the additional benefit of buffering the carbonylate solution at a pH of 7-9, insufficient for $Co(OH)_2$ to form and precipitate. This brings an additional benefit, in that it avoids the excess caustic to react with carbon monoxide to form sodium formate, which would otherwise end up increasing the Biological Oxygen Demand (BOD) emissions in the waste stream by itself or by the formic acid formed from it upon acidification, and also reducing the amount of carbon monoxide in the Oxo offgas which may be recycled. The cobalt carbonate is then settled and filtered from the carbonylate stream, or removed by centrifuging, before this is acidified. The process of U.S. Pat. No. 5,130,107 leads to an acidic waste water stream of reduced volume containing much lower levels of $Co^{2+}$, typically below 50 ppm and generally below 20 ppm of Co by weight. As a byproduct, it produces a volume of cobalt solids, primarily consisting of finely divided pink cobalt carbonate powder, which may be sold or even be reused as oxonation catalyst following a suitable catalyst makeup step, some of which are disclosed in U.S. Pat. No. 5,130,107. If the settling and filtering operation is very effective, there should be almost no measurable $Co^{2+}$ present in the carbonylate at the point where it is acidified. Downstream of this cobalt filter, any cobalt that oxidizes from its (−I) valency state, which it has in the sodium cobaltcarbonyl form, to either (0) or (+II) valency, will again increase the $Co^{2+}$ level in the dilute waste acid stream, either directly or through the disproportionation reaction mentioned above, and raise again the burden to remove it before disposal.

The recovery of hydrocobaltcarbonyl from the carbonylate is the second step of the Kuhlmann cycle and is disclosed in U.S. Pat. No. 3,188,351. In the second step of the Kuhlmann cycle, the sodium cobaltcarbonyl in the carbonylate is converted back into the oxonation catalyst hydro cobaltcarbonyl by acidification of the carbonylate with dilute sulphuric acid. The volatile hydro cobaltcarbonyl is then stripped from the water by a countercurrent flow of absorbing gas, frequently syngas, which is subsequently passed through an absorber column to recover the hydro cobaltcarbonyl from the stripping gas in an absorber liquid suitable for routing to the oxo reaction. Feed olefin is often very suitable, but depending on its nature not always appropriate because of its volatility or structure causing possible side reactions. Other candidates are for example the heavy byproducts from the hydroformylation reaction, part of the product from the hydroformylation or from the downstream hydrogenation reaction, the light oxonation fraction that is separated from the hydroformylation product or from the product alcohol, or the product alcohol itself. In fact, any organic liquid that does not impair the process in terms of chemistry, separations or product quality would be suitable. Olefin feed is the preferred absorbent because it is at the same time a reagent for the hydroformylation reaction. Therefore, alternatives are typically only chosen if the olefin feed is unsuitable as absorber liquid because of e.g. high volatility.

This process makes use of the affinity of $HCo(CO)_4$ for the gas phase as compared to the acid water. In U.S. Pat. No.

3,188,351 we are told that the sulfuric acid is usually supplied in concentrated form, typically 98% by weight, which is then diluted using dilute acid recycling from the $HCo(CO)_4$ removal step and is dosed such that its concentration at the inlet of the volatilisation tower is held from 40 to 100 g $H_2SO_4$ per liter, and at the outlet from 5 to 40 g $H_2SO_4$ per liter. However, in the Example a solution containing 34 g $H_2SO_4$ per liter is used at the inlet of the volatilisation tower where it is brought in contact with the carbonylate. The volatile $HCo(CO)_4$, entrained with the stripping gas, may then be absorbed in an organic liquid suitable for recycle to the hydroformylation reaction, preferably feed olefin, in an absorber tower. This step makes use of the high affinity of $HCo(CO)_4$ for an organic phase, especially for olefins. U.S. Pat. No. 5,130,107 also uses this technique. U.S. Pat. No. 3,188,351 requires that the cobalt hydrocarbonyl, released by acidification of the carbonylate, be removed in the gaseous phase, although it suggests that, during the transfer of the free cobalt hydrocarbonyl into the olefins or organic solvent, it is also possible to put the latter directly into contact with the acidulated aqueous solution.

The technique for recovery of $Co^{-1}$ described in U.S. Pat. No. 3,188,351 suffers from the following disadvantages:

Large volumes of sulphuric acid are used in relation to the cobalt present in the carbonylate, this in turn requires large volumes of alkali for subsequent neutralization. Both these factors require the handling of large volumes of materials.

Despite the use of the large volumes of sulphuric acid, the concentration of acid at the point where it is mixed with the carbonylate, meaning the theoretical concentration after mixing but before any reaction has taken place, is relatively low, for example this concentration in Example 1 of U.S. Pat. No. 3,188,351 is only 1.57%.

At the high levels of cobalt concentration in the carbonylate that are realized in current day operations, such as from 20,000 to 30,000 ppm wt, the volumes of materials required and the demands on the volatilisation tower, in order to strip the hydrocobalt carbonyl vapour to obtain a cobalt recovery of 99.7% or greater, are excessive.

U.S. Pat. No. 5,091,599 discloses the use of 16 wt. % sulphuric acid for slowly acidifying a 14000 ppm cobalt containing solution of sodium cobaltcarbonyl ($NaCo(CO)_4$) in water in a batch experiment for the generation of hydro cobaltcarbonyl which then is stripped with $N_2$ and the gas is led to adsorbers for the hydro cobaltcarbonyl. Up to 93.8% of the cobalt in the starting solution was carried over with the stripping gas. U.S. Pat. No. 5,091,599 is concerned with identifying adsorption liquids having suitable cobalt loading potential. We have found that the use of 16 wt. % sulfuric acid is not suitable in a continuous process for acidifying a sodium cobaltcarbonyl solution in water. Such high strengths of sulfuric acid lead to oxidation of part of the cobaltcarbonyl, which causes the formation of $CO_2(CO)_8$. This form of cobalt is insoluble in water and in the absence of an organic phase will crystallize and precipitate. The solids so formed foul the equipment of the continuous process and impair its operating performance. Another problem is that $CO_2(CO)_8$ formed at the acidification point leads to $Co^{2+}$ at a point in the process where recovery of $Co^{2+}$ has become more complex and difficult.

It therefore remains desirable to further improve the recovery of cobalt in these techniques, and to further reduce the amount of cobalt in any waste streams.

SUMMARY OF THE INVENTION

We have now found that these problems may be overcome if the acid concentration at the point of mixing of the acid and the carbonylate is increased, in a controlled manner that avoids excessive acid strengths. Use of the higher acidification level provides significant benefits in relation to the process described in U.S. Pat. No. 3,188,351. Keeping the acid strengths low avoids the problems that would be caused by using the highly concentrated acid solutions described in U.S. Pat. No. 5,091,599. Furthermore, we have found that the controlled increase in the acid concentration at the mix point, combined with liquid extraction of the hydro cobaltcarbonyl that is released by the acidification of the carbonylate is particularly effective with high cobalt containing streams.

The present invention therefore provides a process for the recovery of cobalt from the product of a continuous cobalt catalysed hydroformylation reaction employing an olefinic feed, which recovery process comprises the steps of (i) forming a carbonylate comprising a water soluble salt of a carbonyl of the cobalt hydroformylation catalyst, (ii) acidifying the carbonylate by combining the carbonylate with an aqueous sulfuric acid solution to form a carbonylate/acid mixture, and (iii) removing hydrocobalt carbonyl from the acidified carbonylate, thereby producing a dilute acid effluent, wherein the aqueous sulfuric acid solution used for acidifying the carbonylate has a sulfuric acid concentration of less than 16 wt. % and the acidification step is performed to provide a sulfuric acid concentration in the carbonylate/acid mixture, before any sulfuric acid consuming reaction, of from 2% to 10% by weight, based on the weight of the mixture.

The compound employed in the step of forming the carbonylate may be any suitable compound that is able to react with the hydrocobalt carbonyl catalyst and form a water soluble salt of the cobalt carbonyl. A list of suitable compounds is found in col 4, lines 10-27 of U.S. Pat. No. 3,188,351. Preferred are potassium and particularly sodium containing bases. More preferred are sodium bases, such as sodium carbonate or sodium bicarbonate, in which case the water soluble salt of the cobalt carbonyl is a sodium salt. Most preferred is sodium hydroxide. Thanks to its high water solubility, a concentrated solution of 50 wt. % NaOH may be used, which may then be diluted with water taken from a downstream water washing step. This allows the total amount of water employed in the catalyst cycle to be kept to a minimum, which brings advantages in equipment size and consumption of chemicals.

Instead of sulfuric acid, also other strong mineral acids would be suitable, such as hydrochloric acid or nitric acid, and the concentrations may need to be adapted according to the acid choice. However, these other acids may introduce other problems, such as chloride corrosion or the risk of nitrate-formation, which will then need to be handled. Sulfuric acid is therefore the acid of choice.

The use of excessive acid strengths, and particularly when using sulfuric acid, in the acidification of carbonylate, may show oxidative activity, which leads to the formation of $CO_2(CO)_8$ and subsequently to more Co2+ at locations in the process where this is preferably avoided or minimised. As explained, the $CO_2(CO)_8$ may become solid and cause operational problems, and/or lead to more $Co^{2+}$, which downstream of the acidification of the carbonylate becomes more complex and costly to remove or recover. We therefore prefer the aqueous sulfuric acid solution used for acidifying the carbonylate to have a sulfuric acid concentration of not more than 14 wt. %, more preferably not more than 12 wt. %, even more preferably not more than 10 wt. %, yet more preferably not more than 8 wt. %, most preferably not more than 7 wt. % and typically around 6.5 wt. %.

In order to save on acid consumption, we prefer that a part of the dilute acid effluent from the hydrocobalt carbonyl removal step (iii) is recycled to the acidification step (ii).

DETAILED DESCRIPTION OF THE INVENTION

Figure 1:
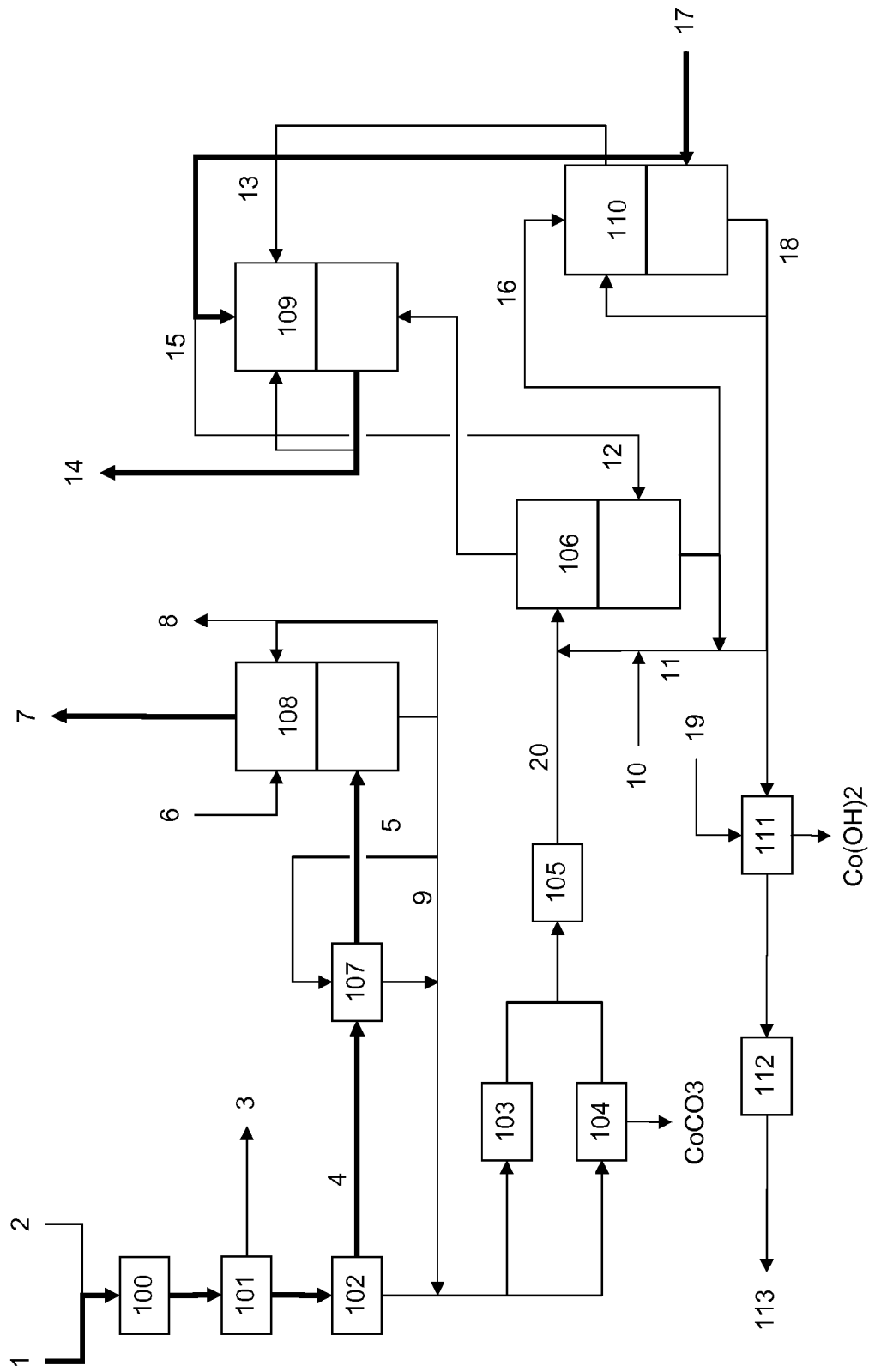
FIG. 1 is a flow diagram illustrating the recovery of cobalt from the product of a typical hydroformylation facility according to the invention.

Due to the immediate reaction of the salts in the carbonylate with the sulfuric acid, the concentration in the carbonylate acid mixture before any sulfuric acid consuming reaction cannot be measured. It is calculated by taking the mass flow (A in kg/hr) of the diluted sulfuric acid directed to the acidification step, and its acid concentration (C in wt. %), and the flow of the carbonylate (B in kg/hr) to the acidification step, and calculating the concentration of the acid in the acidified carbonylate acid mixture (D in wt. %) before any acid is consumed in a chemical reaction, according to the following formula (I):

$$D \text{ (wt. \%)} = A \text{ (kg/hr)} \times C \text{ (wt. \%)}/(A \text{ (kg/hr)} + B \text{ (kg/hr)}) \quad (I)$$

We have found that the acid concentration in the carbonylate/acid mixture, before any sulfuric acid consuming reaction, should be no greater than 10%, and preferably no greater than 8%, since higher acid concentrations can show oxidative activity, which can cause the formation of $Co_2(CO)_8$ which is insoluble in water and in the absence of an organic phase will crystallize and precipitate. The solids so formed may foul the equipment and impair its operating performance. The present invention therefore improves cobalt recovery by minimizing the oxidation of $Co^{-1}$ downstream of the cobalt filter, and thereby maximizing the recovery of $Co^{-1}$ from the carbonylate.

Such oxidative formation of $Co_2(CO)_8$ is also possible, albeit at a lower extent because of the lower cobalt concentrations, in the case when a dilute acid recycle is employed, at the point where the dilute acid recycle is mixed with highly concentrated sulfuric acid, in case the dilute acid recycle contains $HCo(CO)_4$ left over from incomplete recovery of $HCo(CO)_4$ in the second step of the Kuhlmann cycle. Leftover $HCo(CO)_4$ is therefore preferably avoided in the dilute acid recycled for acidifying the carbonylate, before it is mixed with any concentrated acid to bring it again up to its target acid concentration. In the case that leftover $HCo(CO)_4$ is present in the dilute acid recycle, controlling the sulfuric acid concentration in the aqueous sulfuric acid solution used for acidifying the carbonylate according to the invention is helpful in also avoiding problems with oxidation at this mixing point.

Diluting concentrated sulfuric acid is also known to generate a significant amount of heat. When too low amounts of water are used, the temperature of the diluted acid may rise significantly, upon which remaining hydrocobalt carbonyl may become unstable. We therefore prefer that the sulfuric acid concentration in the aqueous solution, immediately after injection of the concentrated sulfuric acid, is at most 16 wt %, preferably at most 14% wt, more preferably at most 12% wt and most preferably at most 10% wt.

We have also found that particularly effective cobalt recovery may be accomplished, if the acid concentration of the present invention is employed with liquid extraction of the liberated hydrocobalt carbonyl.

A liquid/liquid phase extraction system makes use of the affinity of $HCo(CO)_4$ for a liquid organic phase directly. It comprises the direct extraction of $HCo(CO)_4$ from the acidified carbonylate using a suitable organic extraction liquid, preferably the olefinic feed on its way to and employed in the hydroformylation reaction, preferably in a countercurrent liquid/liquid extraction tower representing at least one theoretical extraction stage. The liquid/liquid extraction preferably employs an extraction tower which preferably uses acidification of the carbonylate, partial recycle of acid water over the extraction step, and make up of the strong acid. In order to enhance liquid/liquid contact in the tower, the tower may be compartmented or trayed, and/or be provided with mechanical mixing devices, or the tower may be packed with any commercially available suitable packing material. Because of the high interfacial tension, large size random packing material is preferred, which allows a higher gas flow which improves the liquid/liquid contacting. A limited amount of gas may be bubbled through the liquid-filled tower in order to further enhance mixing of the two liquid phases, in which case the offgas leaving the tower may be contacted with fresh extraction organic liquid to remove any last traces of entrained volatile $HCo(CO)_4$ from it. It is preferred to use a gas containing hydrogen and carbon monoxide, rather than an inert, because the hydrogen affects the cobalt carbonyl equilibrium favorably in the direction of $HCo(CO)_4$, and the carbon monoxide helps to stabilise the cobalt carbonyls. Care must be taken however not to have too much gas present, because this may upset the organic-water phase separations in the tower and cause entrainment of either acidic water into the hydroformylation reaction or of organics with the dilute acid leaving the tower bottom, both entrainments being undesired.

Whilst vapor extraction can be used, the use of liquid/liquid extraction is preferred to vapor extraction because it does not need a gas recycle and it can combine all operations into one single tower.

If a vapor phase extraction step is used, it is performed in a volatilisation or stripping tower. The vapor phase extraction step thus produces a cobalt containing vapor phase, which typically is routed to an absorption step, wherein cobalt is absorbed from the cobalt containing vapor phase into an organic liquid. We prefer to use as organic absorption liquid at least part of the olefin feed employed in the hydroformylation reaction. With more volatile olefin feeds, a heavier organic liquid may be preferable.

The liquid/liquid extraction phase transfer is also found to be more effective than the stripping with gas, thus needing fewer theoretical stages to achieve the same performance. It however brings the drawback that some of the cobalt carbonyls may disproportionate inside the extraction tower, leading to $Co^{2+}$, which is not recoverable at this stage in the process and may need to be handled downstream.

In operation of the present invention, care must be taken of the following aspects.

$HCo(CO)_4$, concentration must be controlled. If the concentrations, either in the water phase, in the vapour phase or in an organic phase, are too high, the material can become unstable and may dimerize to form hydrogen and $Co_2(CO)_8$, which can precipitate out and foul the equipment. This is more likely to occur at lower temperatures, and hence higher temperatures, such as minimum 35° C. or 40° C. are preferred.

Stability of the cobaltcarbonyls is preferably maintained where possible, so that formation of solids is minimised. For this reason it is preferred that a minimum partial pressure of carbon monoxide is maintained in the equipment where $HCo(CO)_4$ is present. When a volatilisation tower is used, many gasses could be used for the stripping, such as nitrogen or methane, but typically a CO/$H_2$ mixture is used for stripping, and the gas composition is preferably controlled by proper purging of inerts, in particular of carbon dioxide. The volume of gas purged from the stripping gas cycle may be made up using fresh syngas. It is advantageous to operate this stripping gas cycle at a pressure sufficient for the gas purge to be utilised as fuel gas, such as 0.8 bar gauge. Where a liquid/liquid extraction tower is used, sufficient CO partial pressure may be assured by using a sufficient amount of a CO-containing gas for bubbling through the liquid-filled tower.

Where a vapor phase extraction step or a volatilisation tower is used, it is preferred that it operates at a temperature higher than the absorption step or absorber tower, otherwise organics in the gas recycled from the absorber to the volatilisation tower may condense in the volatilisation tower, thereby providing an organic liquid phase in which $HCo(CO)_4$ is able to collect and form $Co_2(CO)_8$, and an interface that enables the disproportionation reaction, causing partial conversion of cobalt to $Co^{2+}$, which is not easily recoverable. On the other hand, if the volatilisation tower operates at a higher temperature than the absorber tower, water vaporising in the volatilisation tower and condensing in the absorber bottom may build a separate water phase in that tower, which provides an interface for the disproportionation reaction, and hence formation of undesired $Co^{2+}$. Such a separate water phase may not be desirable in the hydroformylation reactor, and therefore may need to be separated before routing the organics to the oxo reactors, and it may need to be treated for its contained cobalt. This burden is typically easier to handle than the former one of liquid organics in the volatilisation tower, so it is typically preferred to operate the vapour extraction step at a higher temperature than the absorption step.

Where a volatilisation tower is used, sufficient stripping gas needs to be applied for stripping the volatile cobalt from the acidified carbonylate. The rates of stripping gas are preferably at least 100 $Nm^3$ per hour per ton of liquid flowing down the volatilisation tower, more preferably from 120 to 150 $Nm^3$ on the same basis. Typically this stripping gas is at least partly recycled for efficiency from the absorber where its cobalt is removed into the organic absorption liquid. Where carbon dioxide evolves from the carbonylate upon acidification, its concentration in the stripping gas is typically controlled at around 6 mole %.

When lower molecular weight and less branched olefins are used as the absorber liquid in an absorber-volatilisation tower setup, these olefins can undergo chemical complexation with the $HCo(CO)_4$, which can lead to the undesirable formation of $Co_2(CO)_8$. If the absorber tower temperatures are rather high, and CO partial pressures are low, this may lead to cobalt cluster formation and precipitation thereof. This is another reason to prefer a minimum partial pressure of CO where olefin with cobalt is present.

When employing the liquid/liquid extraction care must be taken to control the following aspects.

In spite of its higher efficiency, extraction of $HCo(CO)_4$ from the acidic water stream may still not be fully complete, in particular when cobalt catalyst circulation rates are high.

The water-oil interface enables the disproportionation reaction and any cobalt converting to $Co^{2+}$ is lost from the primary cobalt cycle.

Significant amounts of gas may evolve from the carbonylate at the point of acidification, for instance carbon dioxide due to a significant presence of sodium (bi) carbonate in the carbonylate. Also these gasses can upset the organic-water phase separations.

When linear olefins are used as the organic liquid, the cobalt carbonyl degrading reactions tend to run faster, and more $Co^{2+}$ is typically found in the bottom of the extraction tower. These levels may then reach 150 or 300 ppm by weight, and may under certain circumstances go up to 1000 ppm or more.

Accordingly, preferred aspects of the present invention which help control these issues, employ one or more of the following features.

(i) controlling the acid concentration in the acidified carbonylate, before accounting for any acid consuming reaction, to below 10 wt. %, preferably below 8 wt. %, more preferably below 7 wt. %, and most preferably below 6.5 wt. %. This reduces or eliminates oxidation of $Co^{-1}$ by high acid concentrations. The acid concentration after removal of the hydrocobalt carbonyl typically is controlled at 2 or 2.5 to 4 wt. %, typically at about 3.5 wt. %. With highly reactive olefins, this may be down to 1 or 1.5 wt. %. Lower acid concentrations also mean lower chemicals use, hence a more cost effective operation.

(ii) the acid stream exiting a liquid/liquid extraction step or tower, or a volatilisation step or tower may be subjected to a further cobalt extraction technique for example by extraction with an organic liquid in an extraction step or tower. This provides a mechanism for recovering any remaining unextracted or unstripped $Co^{-1}$ from the first step effluent, and allows the first step to handle much higher cobalt circulation rates, because it is not required to provide by itself the high recovery efficiencies necessary to achieve the low cobalt levels that are ultimately required. In this case, the first step, e.g. a volatilisation tower, and the second step, e.g. an extraction tower, may run on a combined acid recycle over both units into the acidification step, i.e. a so-called "long" acid recycle, so that concentration of $Co^{-1}$ in the dilute acid return is kept low, and hence the risk of oxidation at the injection point of the concentrated sulfuric acid is also reduced. We prefer in such a process scheme to inject any concentrated sulfuric acid into the "long" recycle stream, before any "short" acid recycle over only the first extraction step is added. This minimizes the risk of contacting remaining $Co^{-1}$ with the concentrated sulfuric acid. If hydraulics permit, this "long" recycle over the two steps may be the only acid recycle, which is preferred. If hydraulics for the two steps are very different, each step or tower, or one of them, may still have a (partial) "short" acid recycle over itself. The operation with a volatilisation tower upstream is particularly suitable if there is carbon dioxide present in the decobalter. Such an extra downstream extraction technique also allows the process to run with somewhat lower acid concentrations in the volatilisation step or tower effluent, such as only 1.5% or 2% by weight, and hence consume less chemicals.

(iii) where a volatilisation tower is used, the higher presence of sodium (bi)carbonate in the carbonylate being fed to the volatilisation tower provides more free gas at the acidification point, reducing the concentrations of $HCo(CO)_4$ in the gas and in the water phase, thereby minimising and even avoiding its oxidative dimerisation. This can be achieved by operating the decobalter upstream of the volatilisation tower with a higher excess of soda ash, or caustic soda combined with a sufficient presence of carbon dioxide, relative to the amount of cobalt present. In particular with the acidification of the carbonylate performed upstream and not inside the volatilisation tower, this sodium (bi)carbonate excess is conveniently at least 50%, preferably 100%, more preferably in the range from 150% to 200% on a molar basis relative to the amount of cobalt present. A molar excess of 250% is typically not exceeded, in order to avoid excessive chemicals costs.

This molar excess can be determined by the following analysis to be performed on the carbonylate. First the total cobalt concentration is determined using a standard analysis technique. Subsequently a known weight of filtered carbonylate, from which all cobalt carbonate is removed by filtration, is put in a closed system with a metering device for measuring any volume increase from gas evolution. Using dilute (2% wt) sulfuric acid, the pH is then reduced to around 5. All $CO_2$ present as sodium (bi)carbonate is liberated and the volume of this liberated $CO_2$ is measured. This pH is too high still for any $HCo(CO)_4$ to evolve. In a second step, a suitable amount of hydrocarbon (olefin and/or paraffin) is introduced, and using dilute sulfuric acid of somewhat higher strength, the carbonylate is further acidified to about 2% wt of free sulfuric acid. The amount of acid needed can be calculated from the total cobalt analysis (assuming all cobalt is present as sodium cobaltcarbonyl, thus neglecting any $Co^{2+}$). So far the manipulation needs to be done under inert atmosphere to avoid any oxidation of cobalt. Upon good mixing and subsequent separation of the two phases, the remaining acid solution can be analysed for total cobalt (now only giving the amount of $Co^{2+}$ that was present), for total sodium (by e.g. atomic absorption spectroscopy (AAS), and by high-performance liquid chromatography (HPLC) or potentiometric titration also for the amount of formic acid, as the pKa of formic acid is in between the two pKa's of sulfuric acid. By keeping track of the amount of reagents added, the analytical results can be calculated back to the starting carbonylate. This analysis of the carbonylate results in the total sodium content and its split over the different salts (cobaltcarbonyl, formate, (bi)carbonate), and in the total cobalt content and its split over the different forms (cobalt carbonylate and $Co^{2+}$). The amount of sodium as sodium (bi)carbonate on a molar basis relative to the amount of cobalt present can then be calculated. The method corrects for any formic acid present.

(iv) acidifying the carbonylate only when it is already inside the volatilisation tower, so that the $HCo(CO)_4$ can be immediately extracted by the gas. Care must be taken with regard to carbon dioxide liberating from the liquid and any potential froth forming as a result of that. This froth may cause entrainment of acid liquid into the absorber tower. In such a setup, the upstream decobalter may preferably be operated at a lower excess base and/or a lower presence of $CO_2$, which may also reduce the consumption of chemicals of the overall catalyst cycle.

(v) in a system which employs a liquid/liquid extraction step or an extraction tower, a lower concentration of sodium (bi)carbonate in the carbonylate, being fed to the extraction step or tower, is preferred to avoid upsets of the phase separations in the extraction process. This can be achieved by operating the decobalter upstream of the extraction step or tower with a limited excess of soda ash, or with caustic soda and less or no carbon dioxide present in the decobalter. The molar excess of sodium (bi-) carbonate relative to the amount of cobalt present is typically not more than 70%, preferably max 50%, more preferably 30%, even more preferably max 20%, and most preferably zero. This molar excess can be determined using the analysis explained under (iii) above.

(vi) when a volatilisation tower or vapour extraction step is used, it is preferred to operate the associated absorber step or tower top at a temperature as low as practically possible, preferably at most 40° C., typically from 10 to 30° C., preferably around 20° C., and significantly lower than the vapor extraction step or the volatilisation tower bottom. This is in order to avoid organic vapors condensing in the extraction step or the volatilisation tower. Low temperatures in the absorber step or tower also enhance the absorption of hydrocobalt carbonyl, and minimise the formation of dicobalt octacarbonyl, cobalt clusters and solids. The temperature in the vapor extraction step or volatilisation tower is therefore preferably controlled at 25 to 40° C., typically 10 to 30° C. above that of the absorber step or tower, preferably 12 to 20° C., most preferably about 15° C. above it.

(vii) adding a liquid/liquid extraction step or tower upstream of a volatilisation tower either instead of or in addition to providing an extraction step or tower downstream of the volatilisation tower as per (ii) above. An upstream extraction step or tower can operate as a short contact time pre-extraction tower, which, due to the highly favorable preference of the $Co^{-1}$ for the organic phase, can perform a substantial amount of the cobalt recovery, significantly reducing the demands on the volatilisation tower duty.

(viii) adding a single stage liquid/liquid extraction step upstream of a multistage volatilisation tower or liquid/liquid extraction tower.

The single stage liquid/liquid extraction step in (viii), and/or the equivalent step or tower in (vii), preferably use fresh olefin (or absorption organic) to absorb the cobalt, so that the full absorption potential of the organic phase can be utilised at the point where the supply of cobalt in the acidified carbonylate is at its highest. The organic liquid employed in these liquid/liquid extraction steps preferably comprises at least part of the organic liquid coming from or going to the absorption step.

We have found that, by employing one or more of these techniques in combination with the employment of the acid concentrations of the present invention, the cobalt content of the waste water stream from a cobalt catalysed hydroformylation reaction may be reduced to below 10 ppm, preferably below 3 ppm, more preferably below 1 ppm, and most preferably below 0.5 ppm by weight. We have also found that a tail end biological oxidation (BIOX) treatment on cobalt containing water contributes further to the reduction of the cobalt content, even if the cobalt is in the form of sodium cobalt carbonyl. Through oxidation and adsorption in the biomass or sludge, low cobalt levels of 1-2 ppm wt may further be reduced to 0-1 ppm by wt.

The hydroformylation is typically performed at elevated temperature and pressure in the presence of a hydroformylation catalyst. The optimum temperature and pressure will depend upon the nature of the olefin feed, both in terms of the carbon number(s) of the olefins, the structure of the olefin (linear or branched, branch structure, location of the olefinic bond) and the concentration of the olefin in the feed. The feed is typically a mixture of saturated and unsaturated (predominantly olefinic) materials. Typical pressures are from 50 to 350 barg, preferably 150 or 250 to 350 barg, most preferably from 275 to 325 barg. Typical temperatures range from 120 to 185 or 190° C., preferably from 165 or 170 to 180 or 185° C., although certain olefin feeds may preferably be hydroformylated at lower temperatures such as from 100 or 120 to 140° C. for reasons of olefin reactivity or reaction selectivity. Typically cobalt concentrations of up to 0.8 wt. % cobalt on the olefin content of the feed are used, preferably from 0.02 or 0.05 wt. % to 0.8 wt. % cobalt, more preferably from 0.1 wt. % to 0.5 wt. %.

We have found that hydroformylation processes using catalyst cycles that recycle the cobalt catalyst in its (−1) oxidation state to the hydroformylation reaction, such as the Kuhlmann catalyst cycle, have a particular advantage. These processes are particularly tolerant to feeds containing dienes, more particularly conjugated dienes. We have found that these processes are able to process feeds with significant amounts of dienes, even conjugated dienes. We have found that such processes are able to process feeds containing dienes at concentrations up to 5% wt, such as C5 raffinate streams from isoprene extraction unit, of which the typical olefin content is 50% wt, and diene levels may be as high as 3 or even 3.5% wt. On higher molecular weight streams, this acceptable diene level is even higher. We have found that those processes wherein the cobalt catalyst needs to be converted to its active carbonyl form in the presence of its olefin feedstock, are impaired when dienes are present in the feedstock. This is because the dienes, particularly conjugated dienes, appear to significantly reduce the so-called cobalt preforming reaction, wherein cobalt is converted from its starting compound, such as cobalt oxide or cobalt salt such as formate or acetate, to its active carbonyl form. In those hydroformylation processes, we prefer to operate with an amount of dienes in the feed that is not higher, on a stoichiometric basis, than the amount of cobalt that is fed to the hydroformylation reaction. We therefore prefer the dienes in the feed to these diene-sensitive processes to be at most at the same molar level as the amount of cobalt in the feed, preferably at most 0.2 times, more preferably at most 0.1 times the molar amount of the cobalt in the feed.

The catalyst may be supplied already absorbed in the olefin feed and/or as fresh catalyst. It is preferably supplied absorbed in the olefin feed. The initial cobalt species is preferably cobalt oxide or hydroxide or carbonate. This cobalt source may be preformed in a separate reactor in order to convert it to the carbonyl form, or this conversion may occur in the hydroformylation reactor itself.

We prefer to perform the preforming reaction in a separate reactor, and by using cobalt oxide as the starting material. Cobalt oxide has the advantage of being highly concentrated in cobalt (72% wt) and, upon preforming, leaves only a small and harmless amount of water as byproduct. The cobalt oxide is obtained in powder form, and we prefer to operate with a continuous feed of this powder, as a slurry into an organic liquid such as the olefin feed or a recycle of heavy byproducts from the alcohol manufacturing, into the preforming reactor. We prefer to use colloid mills as part of this cobalt feed, because it increases the tolerance to a broader particle size distribution and to particle agglomeration. We prefer to work with crystalline (recrystallized) cobalt oxide, as it preforms better than the amorphous from, typically coming from spray drying or flame burning. We have also found that the cobalt solids recovered in the Kuhlmann catalyst cycle, such as the cobalt carbonate recovered from the carbonylate, or the cobalt hydroxide recovered further downstream, may be calcined and its cobalt reclaimed as cobalt oxide feed to the preformer reaction. The cobalt particles may even be recycled to the preformer after calcination, thereby avoiding the cobalt reclaiming step. As a result, the ultimate cobalt losses, and thus emissions, from an alcohol plant using the Kuhlmann catalyst cycle can be reduced to the very low levels of 0.5 or even 0.1 kg/day, and this for very high cobalt circulations.

Under the hydroformylation conditions, an equilibrium is believed to establish itself between two cobaltcarbonyls:

$$2HCo(CO)_4 \leftrightarrow Co_2(CO)_8 + H_2$$

Hydr(id)ocobalt(tetra)carbonyl ($HCo(CO)_4$) is generally believed to be the active catalyst form or at least the precursor to the active catalyst form, which also may be $HCo(CO)_3$. The higher the hydrogen partial pressure in the hydroformylation reaction and the higher the temperature, the greater the concentration of hydrocobalt carbonyl, and hence the greater the reaction rate.

Dicobaltoctacarbonyl, under influence of higher temperature and/or lower partial pressures of carbon monoxide, may split off carbon monoxide and form cobalt cluster forms that gradually contain more cobalt and fewer carbonyl functions, and which are less and less soluble in the reaction medium, up to the point where the cobalt compounds come out of solution in forms that contain little carbon monoxide and approach the state of cobalt metal or are metallic. This phenomenon is referred to as "cobalt plating". These cobalt clusters and lower carbonyl containing forms of cobalt are essentially inactive for the hydroformylation reaction. It is well known that at a given temperature and cobalt concentration, a certain partial pressure of carbon monoxide is required in order to maintain the stability of the cobaltcarbonyls, and to prevent the cobalt from coming out of solution and depositing inside the equipment. Cobalt plating requires extensive cleaning of the reactor with for example nitric acid, requiring that the reactor be taken out of service. Sometimes the equipment has to be replaced.

The design of the hydroformylation reactors is therefore targeted, and the conditions of the hydroformylation reaction are therefore controlled, to minimize fluctuations in the reaction temperature, which can cause variations in the product formed and cobalt plating. Temperature control is also important for safety purposes to prevent reaction instability. Accordingly, in addition to optimising gas utilisation and careful management of the gas profile the process described in WO 2005/058787 helps to optimise the reaction temperature with the beneficial effects of increasing reaction yield and minimising or eliminating the plating out of the cobalt within the reactor, which can occur if the reaction temperature is too high. Recycling gas to the reactor in the second position as described in WO 2005/058787 provides a means for providing more free gas and/or more hydrogen to the second and any subsequent reactors, without having to push all the gas and/or hydrogen through the reactor or reactors in the lead position, where extra gas may cause hydraulic or hydrodynamic and temperature instabilities.

The ratio of hydrogen to carbon monoxide in the fresh syngas is typically about 1.3:1, since at this ratio the plating out of the cobalt is substantially avoided, or sufficiently low to be acceptable. However, due to the reaction in the first reactor, where there is some conversion of olefins to aldehydes and alcohols, there will be a change in the ratio of hydrogen to carbon monoxide depending on the degree of conversion to alcohol or aldehyde. This is because the conversion to alcohol requires twice as much hydrogen as is used in the formation of an aldehyde. Accordingly, it may be necessary to replenish the hydrogen level in the second and perhaps subsequent reactors (if used) and this can be accomplished by balancing the composition of the recycle gases and/or by introducing unreacted gasses from the downstream hydrogenation reactor, used to convert aldehydes in the final product of hydroformylation into alcohols. When linear olefins are being processed a lower ratio of hydrogen to carbon monoxide in the first reactor, such as 1:1 or 1.1:1 may be preferred.

The hydroformylation reactors are preferably continuous reactors, which are preferably gas-lift reactors like those described in U.S. Pat. No. 3,830,846, U.S. Pat. No. 4,320,237, WO01/14297, GB 1 308 206 and, more preferably, are loop reactors such as those described in U.S. Pat. No. 4,312,837 by R. Papp, U.S. Pat. No. 4,379,124, or WO97/29018. The reactors are provided with cooling coils and/or conditioners, and/or jackets for temperature control, and it is preferred that the materials be introduced at the bottom of the reactors and are taken off primarily at the top of the reactors, whilst the material not taken off is recycled around the internal or external reactor loop and optionally cooled. Accordingly in a preferred hydroformylation process syngas, olefin potentially containing dissolved or entrained cobalt, potentially water or a hydrocarbon stream containing cobalt, and optionally recycle gas is fed to the bottom of the first reactor, the reaction product is taken off at the top of the first reactor and is then fed to the bottom of a second reactor where it is mixed with fresh olefin, with or without cobalt, and fresh syngas and/or recycle gas. The reaction product is then taken off at the top of the second reactor. In a preferred reaction system the reaction product from the second reactor is fed to the bottom of a third reactor where it is mixed with optionally more fresh syngas and/or recycle gas. This reaction product is then taken off at the top of the third reactor. In a further embodiment the product from the third reactor is then fed to the bottom of a fourth reactor and the final hydroformylation reaction product taken off at the top of the fourth reactor. All reactors in the series can be gas-lift reactors, or loop reactors. If not, only the reactors in the first position and optionally those in second and/or third position may be gas-lift reactors, and the remainder may be vertical tubular reactors as explained above. Reactors may also be arranged in a parallel setup, which is particularly advantageous for lead reactors.

We have found that the design of a hydroformylation loop reactor is important in obtaining a more isothermal temperature profile and in avoiding operating conditions of hydraulic, hydrodynamic and/or temperature instabilities, which may in particular occur at higher feed rates. We prefer the loop reactor to have an upward leg that has at least the same, but preferably a larger diameter than the downward leg, i.e. the part of the downward leg other than the conditioner. We prefer that also the top and bottom bends have this larger diameter. We prefer this larger diameter to be at least 1.1, preferably at least 1.15 or 1.2, more preferably at least 1.4 or 1.5, even more preferably at least 1.6 and most preferably at least 1.75 times the diameter of the downward leg. This design increases reactor volume while maximising two-phase flow stability in the downcomer part of the loop reactor. The reactor in the lead position is more stable when the olefin conversion conveniently reaches a level of at least 50 or 55%, preferably at least 65 or 70%, more preferably at least 75, 80 or even 85%, and most preferably at least 90%.

For curvature of the bends, we prefer to have a bend curvature that is from 2 to 4 times, more preferably about 3 times the diameter of the bend pipe, in order to minimize pressure drop over the bend and maximise circulation rate.

The conditioner is another important element of the reactor design. We have found that the optimal internal diameter of the conditioner tubes, maximising heat transfer area while minimising pressure drop on the tube side, is between 40 and 60 mm, preferably 45-46 mm. For a loop reactor with a height of 40 m, we prefer the conditioner tubes to have a length of at least about 17 m. We prefer different loop reactor sections to be interchangeable, i.e. of the same diameter and length. This reduces the requirement for keeping spare parts in inventory. If some or all the reactor pipe sections have the same length as a conditioner including the two cones that connect to the adjacent reactor sections, this allows for a conditioner that needs cleaning or repair to be temporarily replaced by a reactor pipe section, which may then be operated at a lower throughput rate.

The number of tubes in a conditioner is typically determined by the heat transfer area requirement, by the selected tube length, and by the allowable diameter of the tube sheet. The allowable diameter of the heat exchanger tube sheet is preferably selected such that the transition cones connecting the heat exchanger to the piping of the downward leg and to the bottom bend meet the following criteria. The angle of the wall of the cone at the inlet of the conditioner may be important, because it preferably is such that the risk for backward flow along the wall is reduced. We prefer to provide a cone with a wall angle, with respect to the cone axis in the direction of the flow, that is not more than 12 degrees, preferably not more than 10 degrees, more preferably not more than 9 degrees, and most preferably not more than 6 degrees (having 360 degrees in a full circle). The length of the cone then becomes a result of the compromise of the other reactor design parameters. A final adjustment may then be made by adding some height to the reactor pipe sections and to the overall reactor height such that interchangeability of different sections remains. This also provides additional gas lift that may compensate for the additional pressure drop caused by the lengthening of the conditioner tubes. The selection of the final dimensions can be an iterative process to achieve compliance with the important constraints listed above.

We have found that this loop reactor design makes it possible to reach a much better volumetric efficiency than those disclosed in FR 2 430 764 or U.S. Pat. No. 4,312,837 by R. Papp.

Many construction materials have been used in fabricating hydroformylation reactors. In particular for the high pressure processes, the strength requirements are demanding. With injection of water into the hydroformylation reaction for reaction selectivity or catalyst supply reasons, also corrosion resistance is required. This has led to reactor designs that couple high strength steels as the main construction material, with an internal lining of a higher quality stainless steel, providing corrosion resistance where contact is made with the process medium. Duplex stainless steel, with an austenitic-ferritic microstructure and containing by weight 22-23% Cr, 4.5-6.5% Ni, 3.0-3.5% Mo, 0.14-0.20% N and maximum 0.025% Al is the preferred material of construction for hydroformylation reactors. This duplex stainless steel meets the required corrosion resistance for the process medium with organic acids, carbon monoxide, hydrogen and hydrocarbons at the high pressures. This duplex stainless steel also enables acid cleaning with for instance a mineral acid, such as nitric acid, to dissolve any cobalt metal that may plate out over time. It is also a suitable construction material in many acidic environments, even with organic acids such as formic acid and/or acetic acid.

We prefer to use loop reactors, as disclosed above. The control of the temperatures in hydroformylation reaction requires appropriate temperature measurements in the reactors. This is typically done using thermocouples which are provided inside standard thermowells which extend from the reactor wall into the process fluid. In high pressure processes, these standard temperature measurement devices suffer from slow responses due to the higher wall thicknesses required.

Cobalt cluster or metal deposition on these thermowells may deteriorate the measurement even further. Therefore the use of flange-ring thermocouples is preferred. Metal sealing rings, such as Destec or Graylock rings, are typically used for sealing the joints between individual pieces of equipment where these are bolted together using flanges. These circular sealing rings may be equipped with a hollow rod crossing the circle of the ring, welded on one side to the ring through which a hole is drilled to provide access for a thermocouple inside the cavity of the rod. On the other side, the rod is closed and preferably only supported longitudinally, so that axial displacement is allowed such as because of thermal expansion. Such a hollow rod may have, for example, an external diameter in the range of 4 to 15 mm, and an internal diameter of only 3 to 5 mm. The small wall thickness provides accurate temperature measurement by the thermocouple inside the rod, and fast response of the measurement to temperature changes in the process fluid. Two or more thermocouples may be provided along the length of the rod, either spread along its full length or only half, so that if desired also a radial temperature profile may be measured.

Our preferred loop reactors comprise an upward leg and a downward leg, connected by two 180° bends. The bottom bend preferably has a vertical and tangential feed nozzle underneath the upward leg for the incoming reagents, and the top bend preferably has a central outlet nozzle at its highest point for the reactor product to exit. We prefer for reactor cooling that a heat exchanger is integrated in the downward leg, preferably in the bottom part of the downward leg. Such an in-line heat exchanger is called a conditioner. In addition, we prefer to have the other parts of the reactor to be provided with a jacket around the outer wall, through which a heat exchange fluid is circulated for additional temperature control. This heat exchange fluid circuit may be combined with the coolant circuit of the conditioner. We have found that tail end reactors in a series of reactors may not need a conditioner, because there is less heat to be removed.

Maintaining a good fluid circulation is important in a hydroformylation reactor, for good temperature control. In a gas-lift reactor, this circulation can be driven without mechanical devices, thereby avoiding the risk for leaks of reactor content through seals and the like, which is very advantageous because of the typically high operating pressures. In a gas-lift reactor, the driving force for circulation is provided by the density difference between the fluid in the upward part of the reactor, where more gas is present and the average fluid density is lower, and the fluid in the downward part of the reactor, where less gas is present and the average fluid density is higher. In a loop reactor, the leg in which the reagents are injected contains more gas, its content therefore moves typically upward, and this leg is called the upward leg. The other leg contains less gas, its content typically moves downward, and this leg is therefore called the downward leg. The circulation rate in a gas-lift reactor is a balance between this driving force and the energy loss by friction of the circulating fluid against the equipment walls.

Even in a well circulating loop reactor, we have found that small temperature differences can be measured between different locations in the reactor, in particular in reactors that are in the lead position and are the most critical, and that these temperature differences can be used to monitor the circulation rate and potentially even obtain a quantitative measure thereof. We therefore prefer to have several temperature measurements inside the loop reactor, preferably of the kind that provides a fast response and more preferably using a high reading frequency. Although they are not essential, the flange-ring thermocouples described above have proven to be very useful for this purpose. We prefer to have a temperature measurement representative for the reactor outlet temperature, and one in the downward leg of the loop reactor, immediately upstream of the conditioner. We have found that the temperature upstream of the conditioner will typically read higher than the reactor outlet temperature. We have also found that this temperature difference is an indication of reactor circulation. We prefer to operate with a temperature difference that is at most 20° C. A temperature difference exceeding 20° C. should be an indicator of insufficient circulation, and a sign of fouling or another type of obstruction to flow inside the reactor. We therefore prefer to decommission a reactor in which such high temperature difference is measured.

We have also found that the reactor outlet temperature of a loop reactor may oscillate with amplitude of 1-2° C. We believe that this is caused by a small oscillation in the circulation rate inside the reactor loop, caused by an oscillating phenomenon in the amount of gas passing from the downward leg through the bottom bend into the upward leg. We believe that the frequency of the temperature oscillation is a measure of circulation rate, and we prefer to operate with an oscillation period of at most 100 seconds, more preferably at most 60 seconds.

When the circulation rate of a gas lift reactor has become too low, as may be determined by any of the above indications, this is typically an indication of fouling, primarily by cobalt plating. In such event, we prefer to decommission the reactor and to clean the reactor by circulating a nitric acid solution through it, which dissolves most of the cobalt containing solids. The resulting waste acid may then be sent to a metal reclaimer to reclaim the cobalt, return it into a form that is suitable for cobalt preforming, and recycle this cobalt to the hydroformylation reaction. This further reduces the overall cobalt losses and the overall environmental load of the process.

In addition to the above temperature measurements, we prefer to measure also the temperature of the reactor fluid at the bottom of the conditioner, and also at the mix point where the reagents are introduced into the reactor. We have found that under certain hydraulic conditions, the reactor circulation may stop for short periods, and even reverse flow may occur. Under these circumstances, one or both of these temperatures may drop significantly, to below the temperature of the heat exchange fluid that enters the cooling circuit of the reactor, and even approach the temperature of the incoming reagents. This observation is an indication of hydrodynamic instability, which may be remedied by either reducing the gas feed to the reactor, or increasing the olefin feed, cobalt concentration, or the reactor operating temperature.

After passing through the hydroformylation reactors the final product of the hydroformylation reaction comprises a mixture of alcohols, aldehydes, unreacted olefins, paraffins, formate esters, and heavy oxo fraction, comprising dimer and higher condensation products such as ethers, esters, acetals, hemi-acetals, ether aldehydes, ether alcohols, etc., hydrogen, carbon monoxide, entrained cobalt and cobalt catalyst residues and inert materials. The product must then be purified and separated into its components and the cobalt recovered and recycled and the waste cobalt minimised.

In order to improve the selectivity of the hydroformylation reaction, water may be injected into the hydroformylation reactors. We have found that the presence of water reduces the formation of formate esters and heavy by-products. When used, water is conveniently injected into the first reactor and may also be injected into the second and subsequent reactors that are used but we have found that this is not always essential. In a gas-lift reactor, the formation of a significant volume of a stagnant free water phase in the bottom can become an impediment or even an obstruction to the circulation of the reactor fluid. Gas-lift reactors from which any free water is continuously removed from the bottom have been described in WO 01/14297. If there is no water removal capability, the quantity of water that is introduced should preferably not exceed, or not exceed by more than 10 or 20%, the solubility of the water in the reaction mixture, to avoid the formation of a stagnant free water phase in the reactor. Some water above the solubility limit may be allowed, as long as fluid velocities are sufficient to keep the water in a dispersed form and circulating. The solubility of water in the reaction mixture depends upon the composition and the temperature of the reaction mixture. We have found that preferably no more than 2 wt. % of water based on the weight of olefin feed is used in the first reactor, and typically from 1.0 wt % to 1.75 wt. % particularly 1.5 wt. % should be used. The weight of the olefin feed is the weight of unsaturated materials in the feed which is typically above 95 wt. % of the feed and frequently about 99 wt. % of the feed. If the volume of the lead reactor is relatively small, and the olefin conversion reached at its outlet is limited, the preferred level of water in its feed may be even lower, such as about 0.6 wt %. Where water is injected into the second reactor, similar considerations may apply depending on the design of the reactor. Due to the different liquid composition in the second reactor, the water solubility may be different in this reactor, and we prefer to use typically a total of 2.5 wt. % water present based on the olefin feed. It needs to be understood that these water levels depend on the olefin type and alcohol product that is processed, due to the different water solubility of the corresponding process streams. It also needs to be understood that the distribution of the water injected depends on the size of the individual reactor stages.

We have found that the injection of water provides a significant improvement in olefin utilisation as well as carbon monoxide utilisation per unit of alcohol produced. The water should be injected into a reactor in a manner that ensures good mixing of the water with the reactants and also prevents large fluctuations in the olefin to water feed ratios.

The purification involves amongst other steps the removal of dissolved and entrained catalyst species from the reaction product which may be recycled for further use. The reaction product is typically a gas liquid mixture at about 175° C. and 275 bar gauge pressure and due to the high pressure certain normally gaseous materials are dissolved or are entrained in the liquid phase. The first step in the purification may be the removal of cobalt at high pressure, and the preferred method is by injection of a dilute base, such as dilute caustic soda and/or sodium carbonate into the reaction product in a decobalter vessel following the final hydroformylation reactor. The dilute base is preferably injected at a temperature close to ambient, preferably at a temperature of from 10 to 60° C., more preferably from 20-50° C. and even more preferably from 30-40° C. We have found that the lower the temperature is in the decobalter, the lower the formic acid make is in this decobalter by the reaction of carbon monoxide with sodium hydroxide, when this is used. We prefer to use sodium hydroxide as the base, because of the higher water solubility, so that less water needs to be introduced as compared to when sodium carbonate or bicarbonate are used. The caustic treatment of the crude oxonation reaction product is preferably carried out using 9-15 wt. % (relative to the weight of crude oxonation product) of a dilute aqueous caustic (NaOH) solution containing from about 2-5 wt. % of NaOH.

The temperature of the caustic treated oxo product is lowered from the typical 140-160° C. to about 30-50° C. by cooling, using e.g. a cooling water heat exchanger. Due to the cooling in the presence of high pressure off-gas, the $CO_2$ tends to dissolve in the liquid phase. The carbonate concentration is effectively enhanced, thereby promoting the precipitation of cobalt (II) carbonate. Preferably in this case, the reaction product from the final reactor is fed to the bottom of the decobalter which is conveniently a long vertical jacketed pipe. In the decobalter the majority of the cobalt is converted into $NaCo(CO)_4$, the water soluble sodium salt of hydrocobaltcarbonyl. If sodium carbonate is used or carbon dioxide is present, a small portion of the cobalt may be converted into solid cobalt carbonate. In the absence of carbon dioxide or sodium carbonate, cobalt may be converted to solid cobalt hydroxide, $Co(OH)_2$. This is much less desired than cobalt carbonate, because it typically forms much smaller particles which are very difficult to settle out or centrifuge out, or much more rapidly plug up any filter device. We have found that the decobalting is more effective if the caustic soda and/or carbonate and the reaction product from the final hydroformylation reactor are introduced into the decobalter in a manner that avoids intensive mixing of the products—we have found that if the oil phase (reaction product) and the water phase (dilute caustic soda) are brought into contact gradually, less cobalt is lost as cobalt carbonate, and more cobalt is converted into the water soluble sodium salt. The two streams are preferably introduced through separate injection nozzles at least one of which has a tapered opening to allow the material to mix only gradually and with minimal turbulence with the stream of the other material. This also minimises the cobalt plating at that point. We have found that the use of a tapered opening, sometimes referred to as a diffuser, for the injection of the reaction product of from 2 to 10° preferably 4 to 8°, most preferably 6° to the axis of the nozzle in the direction of the liquid flow through the nozzle is particularly useful.

The decobalter conditions are such that the neutralisation converts the hydrocobalt carbonyl to sodium cobalt carbonyl. In this way the presence of cobalt in the waste water can be minimised. Preferred conditions, when a volatilisation tower is used downstream, are to use a stoichiometric excess of sodium hydroxide or carbonate above the amount needed for cobalt neutralisation. Expressed relative to the amount of cobalt present in the reaction product of hydroformylation, an excess of 30 to 250%, e.g. 100 to 200% particularly 50 or 100 or 140 to 180% is useful. The decobalter is typically operated at a temperature in the range 125 or 140 to 170° C., preferably 155 to 165° C. The decobalter is typically operated at a pressure in the range of 16.1 to 30.1 MPa (160 to 300 bar gauge). It is preferred that sufficient carbon dioxide and/or carbonate is present in the decobalter to buffer the pH of the water separating downstream. We prefer that the amount of carbon dioxide and/or carbonate present in the decobalter vessel is maintained at a level sufficient to buffer the pH of the water separating downstream in the range of 6.5 to 9.0, preferably in the range 7.8 to 8.5. Further possible embodiments can be found in U.S. Pat. No. 5,130,107. The cobalt containing stream produced by the decobalting of the hydroformylation product is then subjected to the cobalt recovery techniques of the present invention.

The decobalted hydroformylation product, combined with the separate water phase formed during decobalting, consists of dissolved gas, entrained gas, water, and the hydroformylation product itself. It may be fed, preferably after cooling, to a high pressure separator which separates the free gas from the liquid phase as high pressure offgas. Temperatures of 30-50° C. are preferred because they improve gas/liquid and water/oil separations. Lower temperatures require more complex equipment, increase liquid viscosities to the point they impede oil/water separation, and have an unfavourable effect on the distribution of NaCo(CO)$_4$ between the water and the organic phase. Typically, the high pressure separator operates at a pressure of 250 barg or higher. The gas is separated off and the amount required for recycle is sent to an offgas recycle compressor system. Any excess gas may be disposed of. Such gas purge may be used to control the recycle gas composition. In addition, unwanted gasses such as excess nitrogen and other non-condensables may also at least partially be removed, to ensure that the recycle of gasses according to the present invention does not result in an undesirable build up of inert gasses such as nitrogen in the hydroformylation reactors.

The liquid left in the high pressure separator may then be fed, possibly after cooling, to an intermediate pressure separator where the pressure is reduced to a level that a major portion of the gasses still dissolved and/or entrained in the liquid from the high pressure separator are released as an intermediate pressure offgas. In certain processes it may be useful to employ more than one high pressure separator, in which case two or more intermediate pressure separators may be employed or the liquid products from the high pressure separators may be combined and fed to a single intermediate pressure separator. Here again, any excess gas may be disposed of and unwanted gasses such as methane may be removed.

The pressure in the intermediate pressure separator is typically between 50 and 200 barg, and we have found that a pressure of around 100 barg is particularly useful. The reduction in the pressure releases the dissolved gasses, particularly a part of the unreacted hydrogen and carbon monoxide, and methane, of which a portion can be sent to an offgas recycle compressor system for subsequent recycle. The rest is then typically disposed of as a purge stream.

The pressure of the liquid or liquids from the intermediate pressure separator may then be further reduced and the liquid or liquids may be routed, possibly after cooling, to a low pressure separator and/or to a washing arrangement, where further catalyst values may be extracted from the hydroformylation product by a water stream. This washing arrangement may be one or a sequence of mixing and separation steps, or may be in the form of a countercurrent or cocurrent extraction tower. This step may benefit from being heated or preheated, partly because this extraction/washing step may be associated with chemical reactions like e.g. disproportionation of CO$_2$(CO)$_8$ into so-called Co—Co salt (Co(Co(CO)$_4$)$_2$) and carbon monoxide. The higher temperature also favours NaCo(CO)$_4$ distribution towards the water phase. The preferred embodiment of the invention even includes a heated settler upstream of the wash tower, operating at a temperature of 40, 45 or even 50° C. This provides a more favourable distribution of NaCo(CO)$_4$ towards the water phase and enhances any remaining disproportionation reaction, while preventing any cobalt carbonate solids formed thereby from reaching the washing tower and possibly impairing its operation. Such solids are preferably settled in the settler, or entrained downstream into the solids separating device. This settler is preferably separate and downstream from the low pressure separator in the Oxo back end, which should preferably operate as cold as conveniently possible in order to limit the amount of organic liquids that vaporise and leave with the low pressure offgas. We have found that with an alkaline decobalting process, the further reduction of catalyst values is more effective if the level of sodium in such a washing arrangement is kept low. Fresh water is preferred to the washing step, and the washing step preferably operates with sodium levels in the used wash water of at most 0.5% wt, more preferably at most 0.2% wt, and most preferably at most 0.1% wt. Alternatively, the washing step could make use of recycle water available from a concentrator on the carbonylate, such as an evaporator or a membrane unit.

We prefer a process wherein a step for the removal of cobalt from the process as Co$^{2+}$ is included, typically as Co2+ salts, and preferably by precipitation as cobalt carbonate and/or cobalt hydroxide. The precipitate may be removed by settling, filtering and centrifuging, optionally with the addition of a flocculant.

We prefer to remove the cobalt solids, primarily being in the form of cobalt carbonate, from the carbonylate before it is acidified, by settling and/or filtering or any other suitable means. The alternative is to entrain them into the acid part of the catalyst cycle, in which case the Co$^{2+}$ and any organics also entrained, need to be removed downstream. This brings an extra load on any downstream cleanup processes, such as a Co(OH)$_2$ precipitation and/or filtering step, and/or a biological oxidation (BIOX) unit, where the streams have become larger in volume and more dilute.

The offgasses for recycle from the high pressure and intermediate pressure separators, and optionally a hydrogen stream from the downstream hydrogenation reactor may be fed to one or a set of recycle compressors and, if necessary fresh hydrogen may be added to produce the recycle stream for hydroformylation having the desired composition.

Alternatively, if the downstream hydrogenation process operates at a higher pressure, like 200 barg, the offgas from the hydrogenation unit will also be at a higher pressure, and can be introduced at a point in the recycle gas compression circuit where the pressure is higher, or even directly injected into the preferred points in the hydroformylation process if the hydrogenation pressure is higher than the hydroformylation pressure.

We have also found that the carbon monoxide content of the offgas from the high pressure separator is desirably such that the partial pressure of CO is above 75 barg, better above 77 barg, preferably above 84 barg since if the partial pressure drops below these levels, cobalt plating can occur in the hydroformylation reactors. Similarly, the hydrogen content of the offgas from the high pressure separator should be such that the partial pressure of hydrogen is desirably above 75 barg, better above 77 barg, preferably above 84, more preferably above 91 barg, since if the partial pressure drops below this level there is a drop in reaction rate, and the cobalt equilibrium in the reactors and in the decobalter is less favourable. These issues may be controlled by checking the syngas composition, the total pressure and/or the pressure drop across the hydroformylation reaction and the proportion of inerts in the various streams, and making the appropriate adjustments.

The present invention is useful in recovering cobalt from the cobalt catalysed production of aldehydes and alcohols from any olefins which may be subjected to hydroformylation but is particularly suited to the recovery of cobalt from the product of hydroformylation of C$_4$ to C$_{16}$ preferably C$_4$ to C$_{12}$ olefins for the production of C$_5$ to C$_{13}$ aldehydes and alcohols, in particular C7, C8, C9 or C10 alcohols. The aldehydes may be oxidised to produce C5 to C13 acids, in particular C6, C7, C8 or C9 acids. The acids and the alcohols may be esterified to produce esters. For example, the alcohols may be esterified with an acid or an anhydride, such as phthalic acid or anhydride, benzoic acid, cyclohexanoic acid, cyclohexane dicarboxylic acid, adipic acid, trimellitic acid, pyromellitic acid or any of their anhydride. When the ester is a benzoate or a phthalate, the ester may be further hydrogenated to produce a cyclohexanoate mono- or dicarboxylate ester. Processes for esterification of alcohols and acids are well known in the art, such as those described in WO 2005/021482 or WO 2006/125670. Processes for hydrogenating esters that contain aromatic ring structures are also well known in the art, such as those described in EP 1042273, US 2004/0260113 or WO 2004/046078. The present invention is therefore particularly useful in the production of isononyl- or isodecyl benzoate (INB or IDB), di-isononyl phthalate (DINP) or cyclohexane dicarboxylate (DINDCH), di-isodecyl phthalate (DIDP) or cyclohexanoate (DIDCH).

The process of the invention is illustrated by reference to FIG. 1 in which the product of cobalt catalysed hydroformylation (1) and dilute caustic (2) are contacted in a high pressure decobalter (100). At this stage the product may contain several thousand parts per million by weight of cobalt. The effluents from the decobalting section flow after cooling and high pressure and intermediate pressure gas separation (not shown) into a low pressure gas-liquid separator (101), where offgas (3) is separated. The liquids from separator (101) flow into water product separator (102). The separated organic product (4) is preferably heated (heater not shown), mixed with recycled wash water (5) from tower (108) and sent to a second water product separator (107).

The pH of the water leaving the decobalting section, in FIG. 1 via separator (102), is preferably maintained between 6.5 and 9.0, more preferably from 8.0 to 8.5. At pH values below 6.5, the process cannot remove cobalt (II) from solution, and at pH values above 9.0, cobalt hydroxide will be formed instead of the much more desired cobalt (II) carbonate.

The organic product from separator (107) is fed to wash tower (108), while the water phase is combined with the one from water product separator (102) and sent to settlers (103) and (104).

In wash tower (108) the product is washed with fresh wash water (6) and after separation sent to hydrogenation (7). The used wash water from tower (108) bottoms may sometimes be partly recycled over tower (108) itself, and is partly sent to separator (107) as stream (5), partly used for diluting the caustic injected into the decobalter (8), while the remaining (9) goes to settlers (103) and (104).

In settlers (103) and (104) entrained organic product and solids are separated from the sodium cobalt carbonyl water, also known as carbonylate (20), which is pumped through cobalt solids filter (105) to volatilisation tower (106). The cobalt solids which build up in filter (105) may be regularly backflushed into settlers (103) and (104). The solids may be removed from the settlers before their volume impedes a good settling performance.

Optionally the carbonylate may be concentrated (not shown), by means of an evaporator, a membrane unit or any other suitable method. This may be done before, but preferably after filtering so that no solids are present during the concentration step. Any or a part of the low cobalt containing or cobalt free water that is rejected from such a concentrator may then be reused as fresh water supply to the wash tower (108).

In the volatilisation tower (106) acid, preferably sulphuric acid, (10) is diluted with recycle (11) and added to the sodium cobaltcarbonyl water to produce a mixture containing from 2% to 10% acid before reaction and this reacting mixture is countercurrently stripped with gas (12). For calculating the acid concentration after acidification and before reaction, referring to formula (I), flows (10) and (11), and the acid concentrations thereof may be used to calculate first their combined flow (A) and its acid concentration (C). Alternatively, the combined flow may be measured by a flow meter, and its concentration determined by analysing a sample. By entering the carbonylate flow (20) as (B) in the formula (I), the concentration (D) can then be calculated. The stripping gas containing hydro cobaltcarbonyl leaves the volatilisation tower (106) and passes to absorber tower (109) where it is contacted with oxo feed (13, 17) which will absorb the hydro cobaltcarbonyl and recycle the cobalt catalyst to oxonation via stream (14). The gas coming off at the top of the absorber tower (15) is essentially free of hydro cobaltcarbonyl and then used as the stripping gas for tower (12). Optionally a portion is purged and fresh gas is added to control its composition, primarily its carbon dioxide content. The organic product (14) from the bottom of the absorber tower (109), containing the cobalt, may be fed as a component of the feed to the hydroformylation reaction.

FIG. 1 also shows the provision of an extraction means (110) which may be an extraction drum for further removal of $Co^{-1}$ from the waste water that exits the volatilisation tower (106) and is not recycled (16). This extraction means (110) may also be a multistage countercurrent extraction tower, such as a vertical vessel, optionally compartmented with baffles to delimit the stages, possibly provided with an axial shaft on which rotors or impellers are mounted for assuring good phase mixing, which shaft may be driven by a motor. The water from the volatilisation tower bottom (16) may flow down extraction tower (110) in countercurrent with some of the fresh liquid olefin feed (17) being fed at the bottom of the extraction tower and flowing upward. Typical oil-to-water ratio in such an extraction tower may be about 1 to 1 on a volumetric basis. The olefin collecting at the top of the extraction tower (13) may be fed to the absorber tower (109), preferably not at the top of the tower, where its cobalt concentration may be increased further. More fresh olefin (17) is the preferred organic to be introduced at the top of the absorber tower. Optionally, cobalt containing olefin may be recycled over the absorber tower, however preferably not to its top. This may be done to improve wetting in the tower, or for cobalt concentration buildup. We have found that, using these techniques, the water leaving the extraction tower bottom (18) may not contain any measurable $Co^{-1}$. As shown, this water may be partially recycled to the extraction tower top, as a "short" acid recycle, and partially used to dilute the strong acid (10), as a "long" acid recycle, thereby reducing $Co^{-1}$ concentrations at the point where the fresh strong acid (10) is injected.

The water (18) may however still contain some Co, typically as $Co^{2+}$, and in order to recover this $Co^{2+}$ (present primarily as $CoSO_4$), the rest of this water is brought, using concentrated caustic soda (19), to a pH in the range of 10.5 to 13.0, at which the solubility of $Co(OH)_2$ is the lowest, being in the range of 0.035 to 0.050 ppm by weight of cobalt. The $Co(OH)_2$ precipitates out and forms a sediment in the clarifier (111). Due to the small size of cobalt hydroxide particles, long residence times and typically also addition of a flocculant is highly desirable to ease this sedimentation step. The water from the clarifier may be passed through a filter (112), such as a sand filter, to remove the last traces of cobalt solids. Its pH may then again be reduced to a range between 6 and 9, preferably by using $CO_2$ injection because this is self-buffering, after which it may be routed to a biological oxidation unit (113) for removal of organics, after which it may be discharged. In this way the cobalt level in the discharged water may be reduced to below 10 ppm, preferably below 3 ppm, more preferably below 1 ppm, and most preferably below 0.5 ppm by weight. Cobalt losses to the environment via this waste water may thereby be reduced to below 6 kg/day, preferably below 1.5 kg/day, more preferably to below 0.5 kg/day, most preferably to below 0.1 kg/day for a conventionally sized hydroformylation process.

In one aspect of the invention, the cobalt separation technique involves precipitation of cobalt salts and the presence of carbon dioxide in the high pressure oxo offgas can be used to promote the formation of cobalt carbonate. This may be accomplished by leaving 1-3 volume % carbon dioxide in the fresh synthesis gas as opposed to earlier processes when carbon dioxide has been deliberately removed (to levels of less than 0.1% by volume) from the syngas feed. The carbon dioxide may also be provided, or its level may be further increased, by introducing hydrogen containing 10-20 volume % carbon dioxide into the oxonation section, such as by recycling such a hydrogen stream from a hydrogenation reaction performed downstream of the hydroformylation reaction. This is contrasted to prior art practice where such recycled gas contained less than 0.1% volume of $CO_2$. We have found that contrary to the general belief, the presence of excess carbon dioxide is not harmful to the oxonation process and does not create additional cobalt losses.

An alternative is to use fresh synthesis gas free of carbon dioxide, and to introduce hydrogen containing 10-20 volume % carbon dioxide to the oxonation section, such as explained above.

Cobalt carbonate is less water soluble than cobalt hydroxide, therefore the presence of carbon dioxide in the high pressure oxo offgas is more effective in removing water soluble cobalt (II) species than the addition of excessive amounts of caustic. The carbonate particles are typically also significantly larger than any cobalt hydroxide particles, which are difficult to separate, filter or centrifuge out, and rapidly plug up any filter device for their removal.

Accordingly in a preferred aspect of the present invention, after the product has been washed with a water stream in a wash tower (108), carbon dioxide is injected into the water stream preferably as it leaves the wash tower and passes to the cobalt water storage drums (103) and (104), to further promote the formation of cobalt carbonate. A flocculant, for instance a polymethyl methacrylate, may be injected to facilitate the cobalt carbonate particle growth and the settling in the cobalt water storage drums. An easier method of stimulating cobalt carbonate particle growth is the recycle of wash tower (108) bottoms water back to the decobalters (100) or to the product settlers (102) and (107), since the cobalt species present in this recycle stream enhance the formation of even larger cobalt carbonate particles.

After the formation of the cobalt salts, as much as possible of the solids should be allowed to settle from the carbonylate stream prior to pumping it to the stripper column (106). This may be accomplished by leading the water from the product separation step to the two parallel and/or run in series settlers (103) and (104), which also act as sodium cobalt carbonyl water or "carbonylate" storage drums, and hence as cobalt inventory in the system. These two drums are designed for maximum settling performance and preferably employ a residence time of at least 5 hours, typically a residence time of 5-10 hours. Internals, such as floating suctions, may be installed in the drums to prevent cobalt particles entraining from the drums and to avoid stirring up of the already settled particles. If cylindrical drums are used, they may also be installed in a tilted position to enhance their solid collection capabilities relative to their volume. Another important aspect of maximizing settling times is the reduction of the water flows entering the settlers. This may be achieved by minimizing the net water flow going to the wash column (108), which also proceeds via partly recycling over wash column (108) itself. As is shown, the wash tower bottoms stream may also be used for prewashing the oxo product going to the oxo product separator (107) via line 5.

The cobalt salts must then be physically separated and in our preferred process the settled water containing sodium cobaltcarbonyl is pumped from settlers (103) and (104) to the volatilisation column (106) to liberate hydro cobaltcarbonyl. To minimize the risk of cobalt salts entering this tower, the water stream is preferably first passed through filter (105) to remove any entrained solids. The fresh water from the filter backflushing is sent back to the settler drums. An important aspect of this filter operation is the stability of the water flow to the volatilisation tower (106), which should not be affected by the filter operation.

An alternate way of removing entrained cobalt particles is to pass the water stream via a centrifuge, while avoiding air contact to prevent oxidation of the cobalt carbonyls. The addition of a flocculant may be required for centrifuging, but may also be used in any of the other steps for removal of a precipitate.

The cobalt salts, which settle out in the drums (103) and (104), build up as sludge which requires periodic removal and which may then be recycled. During this removal the watery sludge may be centrifuged or filtered to concentrate the sludge, and the filtrate, being water with dissolved sodium cobalt carbonyl, may be fed back to a suitable point in the process for further recovery of this easily recoverable cobalt according to this invention for eventual reuse in the hydroformylation process.

The recovered cobalt salts, mainly cobalt carbonate but also any other salt such as cobalt hydroxide, can be recycled back to the oxonation (hydroformylation) process as make up catalyst. This may be accomplished by reworking it into cobalt oxide by e.g. roasting which may be performed by the original cobalt supplier. The cobalt oxide may then be recycled to the hydroformylation reaction as make up catalyst. Another method of recycling is to first wash the sludge with a carbon dioxide and/or carbonate containing water stream to remove sodium salts from the sludge and then pump it to the so-called cobalt catalyst preforming reactors to convert the cobalt carbonate into hydro cobaltcarbonyl. Normally these reactors preform cobalt oxide into hydro cobaltcarbonyl. The recycle of the cobalt sludge would not be possible in the conventional process where all $Co^{2+}$ is precipitated under the higher alkaline conditions, since caustic treatment of the acidic waste water stream leads to the formation of a slurry of cobalt hydroxide in an alkaline sodium sulphate solution. This alkaline sodium sulphate solution is difficult to remove without redissolving cobalt hydroxide, while the sodium is undesired in the preformer because it traps valuable cobalt carbonyl, and the sulphate is undesired in hydroformylation because of corrosion and precipitation.

The techniques of the present invention combined with other cobalt recovery techniques described herein have led to a significant reduction of the cobalt losses into the waste water stream from cobalt catalysed hydroformylation. Conventional cobalt recovery techniques for a plant capacity of some 100 kta of alcohol production may result in cobalt losses in the order of 15-30 kg Co/day (based on a monthly average), while after implementation of the invention such losses may be reduced to below 0.5 kg Co/day, typically in the range of 0.02 to 0.10 kg/day during stable operation. At the same time, the average cobalt circulation rate in the hydroformylation reaction may be increased from 30 kg Co/hr to at least some 150 or even 160 kg/hr, which would otherwise have caused a significant increase in cobalt in the waste water. In relative terms, the techniques of the present invention therefore allow a reduction in cobalt losses for such a plant from a value typically in the range of 2-4% on cobalt circulation, down to below 0.0025% on cobalt circulation.

Having now fully described this invention, it will be appreciated by those skilled in the art that the invention can be performed within a wide range of parameters within what is claimed, without departing from the spirit and scope of the invention.

The invention claimed is:

1. A process for the recovery of cobalt from the product of a continuous cobalt catalysed hydroformylation reaction, which recovery process comprises the steps of:
   (i) by a treatment of the hydroformylation product with dilute base forming a carbonylate, comprising a water soluble salt of a carbonyl of the cobalt hydroformylation catalyst,
   (ii) acidifying the carbonylate by combining said carbonylate with an aqueous sulfuric acid solution to form a carbonylate/acid mixture, and
   (iii) recovering hydrocobalt carbonyl from the acidified carbonylate, thereby producing a dilute acid effluent,
wherein the aqueous sulfuric acid solution used for acidifying the carbonylate has a sulfuric acid concentration of less than 16 wt % and the acidification step is performed to provide a sulfuric acid concentration in the carbonylate/acid mixture, before any sulfuric acid consuming reaction, of from 2% to 10% by weight, based on the weight of the mixture.

2. The process according to claim 1 in which the hydrocobalt carbonyl is removed from the acidified carbonylate by at least one stage of liquid/liquid extraction with an organic liquid.

3. The process according to claim 2 in which the water soluble salt comprised in the carbonylate is a sodium salt and the carbonylate being fed to the acidification step contains at most 30% sodium as sodium(bi)carbonate on a molar basis relative to its cobalt content.

4. The process according to claim 1 in which the hydrocobalt carbonyl is removed from the acidified carbonylate by a vapour phase extraction step, thereby producing a cobalt containing vapor phase, followed by an absorption step, wherein cobalt is absorbed from the cobalt containing vapour phase into an organic liquid.

5. The process according to claim 4 in which the absorption step is carried out in a countercurrent absorption tower.

6. The process according to claim 4 in which the water soluble salt comprised in the carbonylate is a sodium salt and the carbonylate being fed to the acidification step contains at least 55% of sodium as sodium(bi)carbonate on a molar basis relative to its cobalt content.

7. The process according to claim 4 in which the vapour phase extraction step is preceded by at least one liquid/liquid extraction step for removing hydrocobalt carbonyl, performed on the acidified carbonylate feed.

8. The process according to claim 4 in which the vapour phase extraction step is followed by at least one liquid/liquid extraction step performed on the dilute acid effluent stream exiting the vapour phase extraction step for removing more hydrocobalt carbonyl.

9. The process according to claim 1 wherein the carbonylate is formed by injection of dilute caustic soda and/or sodium carbonate into the reaction product of the hydroformylation reaction in a decobalter vessel.

10. The process according to claim 1 wherein further comprising a step for the removal of cobalt from the process as $Co^{2+}$.

11. A process for the production of alcohols involving a continuous cobalt catalysed hydroformylation reaction stage wherein the cobalt catalyst is removed from the product of the continuous hydroformylation reaction by the process according to claim 1.

12. A process for producing an ester by esterification of an alcohol with an acid or an anhydride, wherein the alcohol is produced by the process according to claim 11.

13. The process according to claim 12 wherein the acid or anhydride is phthalic acid or anhydride, benzoic acid, cyclohexanoic acid, cyclohexane dicarboxylic acid, adipic acid, trimellitic acid, pyromellitic acid or any of their anhydride.

14. The process according to claim 13 wherein the ester is a benzoate or a phthalate, and the ester is hydrogenated to produce a cyclohexanoate mono- or dicarboxylate ester.

* * * * *